US010219684B2

(12) United States Patent
Onishi

(10) Patent No.: US 10,219,684 B2
(45) Date of Patent: Mar. 5, 2019

(54) ENDOSCOPE REPROCESSOR

(71) Applicant: OLYMPUS CORPORATION, Tokyo (JP)

(72) Inventor: Hideto Onishi, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 112 days.

(21) Appl. No.: 15/424,972

(22) Filed: Feb. 6, 2017

(65) Prior Publication Data
US 2017/0143197 A1 May 25, 2017

Related U.S. Application Data

(63) Continuation of application No. PCT/JP2016/059493, filed on Mar. 24, 2016.

(30) Foreign Application Priority Data

Aug. 24, 2015 (JP) ................................. 2015-164872

(51) Int. Cl.
| | |
|---|---|
| A61B 1/12 | (2006.01) |
| G02B 23/24 | (2006.01) |
| A61B 1/00 | (2006.01) |
| A61L 2/18 | (2006.01) |
| A61L 2/24 | (2006.01) |
| A61B 90/70 | (2016.01) |

(52) U.S. Cl.
CPC .......... *A61B 1/123* (2013.01); *A61B 1/00057* (2013.01); *A61B 1/125* (2013.01); *A61L 2/18* (2013.01); *A61L 2/24* (2013.01); *G02B 23/24* (2013.01); *A61B 2090/701* (2016.02); *A61B 2090/702* (2016.02); *A61L 2202/24* (2013.01)

(58) Field of Classification Search
CPC ....................................................... A61B 1/123
See application file for complete search history.

(56) References Cited

FOREIGN PATENT DOCUMENTS

| | | |
|---|---|---|
| JP | S62-042064 | 3/1987 |
| JP | 2009-172012 A | 8/2009 |
| JP | 2010-057792 A | 3/2010 |
| JP | 2010-057793 A | 3/2010 |
| JP | 5248997 B2 | 7/2013 |

OTHER PUBLICATIONS

Extended Supplementary European Search Report dated Mar. 14, 2018 in European Patent Application No. 16 83 8832.0.

*Primary Examiner* — Jason Y Ko

(74) *Attorney, Agent, or Firm* — Scully, Scott, Murphy & Presser, P.C.

(57) ABSTRACT

An endoscope reprocessor includes: a concentration meter including a housing including a hollow, an osmosis membrane covering the hollow, and internal liquid stored in the hollow; a tank configured to store measurement target liquid and holding the concentration meter so that the osmosis membrane is in contact with the measurement target liquid; a first adjusting portion configured to adjust a pressure of the internal liquid; a second adjusting portion configured to adjust a pressure of the measurement target liquid; a controlling portion configured to control the first adjusting portion and the second adjusting portion.

8 Claims, 7 Drawing Sheets

ENDOSCOPE REPROCESSOR

CROSS REFERENCE TO RELATED APPLICATION

This application is a continuation application of PCT/JP2016/059493 filed on Mar. 24, 2016 and claims benefit of Japanese Application No. 2015-164872 filed in Japan on Aug. 24, 2015, the entire contents of which are incorporated herein by this reference.

BACKGROUND OF INVENTION

1. Field of the Invention

The present invention relates to an endoscope reprocessor provided with a concentration meter using an osmosis membrane.

2. Description of the Related Art

For an endoscope used in a medical field, reprocessing using medicinal solution such as cleaning processing and disinfecting processing is performed after the endoscope is used. Further, an endoscope reprocessor which automatically performs reprocessing of an endoscope is known. For example, in Japanese Patent Application Laid-Open Publication No. 2010-57792, an endoscope reprocessor provided with a concentration meter configured to measure a concentration of measurement target liquid, which is medicinal solution to be used for reprocessing, is disclosed.

As the concentration meter, such that is in a form of using an osmosis membrane causing particular matter in the measurement target liquid to pass through is known. In the case of measuring a concentration of the measurement target liquid using the concentration meter in the form, a measurement face, which is a part where the osmosis membrane is provided, is caused to come into contact with the measurement target liquid.

SUMMARY OF THE INVENTION

An endoscope reprocessor of an aspect of the present invention includes: a concentration meter including a housing including a hollow, an electrode accommodated in the hollow, an osmosis membrane covering the hollow, and internal liquid stored in the hollow and connecting the electrode and the osmosis membrane; a tank configured to store measurement target liquid and attachably and detachably hold the concentration meter so that the osmosis membrane is in contact with the measurement target liquid; a first adjusting portion configured to adjust a pressure of the internal liquid; a second adjusting portion configured to adjust a pressure of the measurement target liquid; a controlling portion configured to control the first adjusting portion and the second adjusting portion to enter a first state in which the pressure of the internal liquid is a first pressure, and the pressure of the measurement target liquid is a second pressure, and a second state in which the pressure of the measurement target liquid is a third pressure lower than the first pressure, and the pressure of the measurement target liquid is a fourth pressure lower than the second pressure; and a maintaining portion configured to maintain the second state for a predetermined time period.

DETAILED DESCRIPTION OF THE PREFERRED EMBODIMENT(S)

Figure 1:
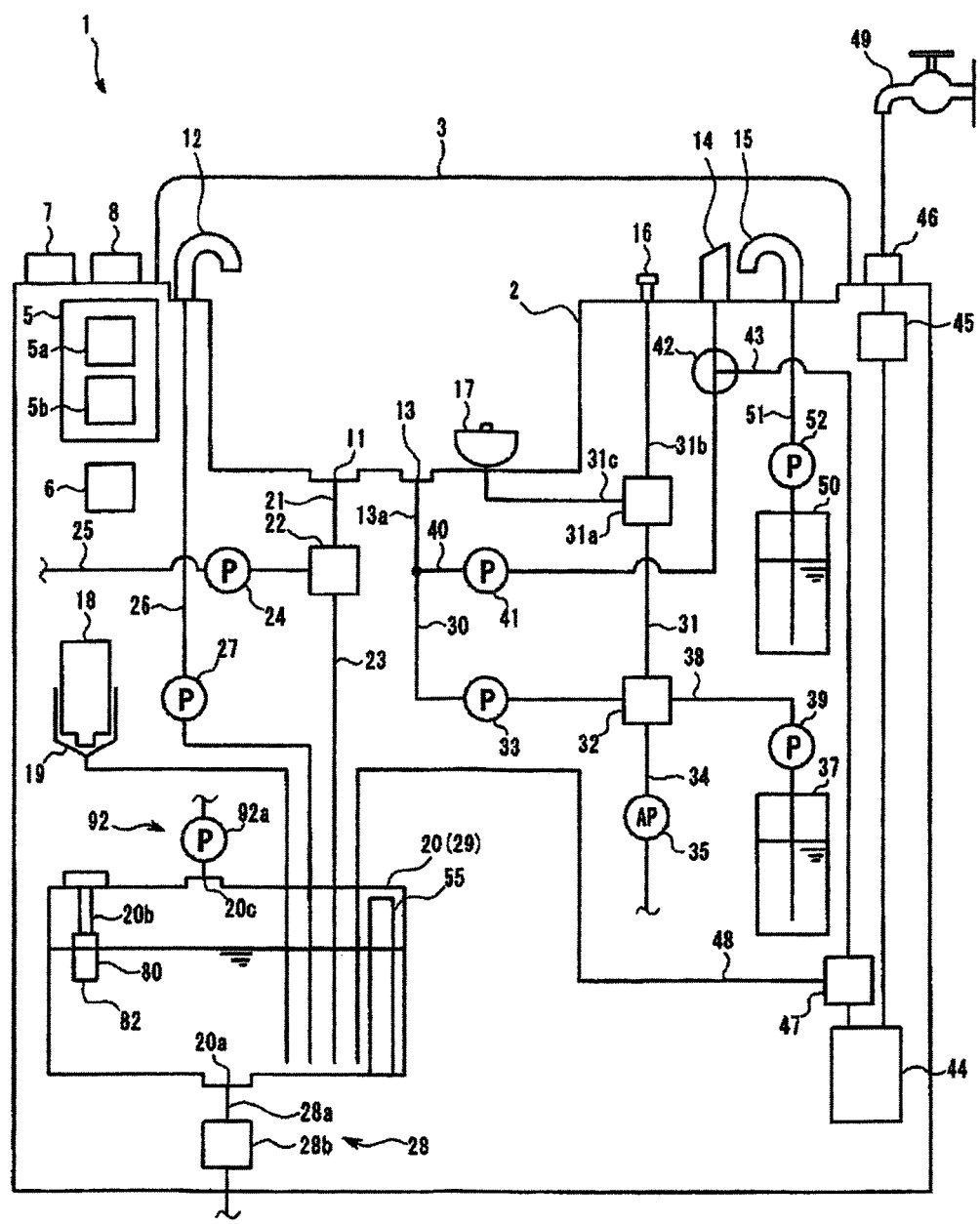
FIG. 1 is a diagram showing a configuration of an endoscope reprocessor of a first embodiment.

Preferable embodiments of the present invention will be described below with reference to drawings. Note that, in each of the drawings used in the description below, a reduced scale of each component is caused to be different so that each of the components is in a recognizable size on the drawing, and the present invention is not limited only to the number of components, shapes of the components, a ratio among sizes of the components, and a relative positional relationship among the respective components illustrated on the drawings.

First Embodiment

An example of embodiments of the present invention will be described below. An endoscope reprocessor 1 shown in FIG. 1 is an apparatus for performing reprocessing for an endoscope. The reprocessing stated here is not especially limited but any of rinse processing with water, cleaning processing for washing out stains such as organic matter, disinfecting processing for disabling predetermined microbes, sterilization processing for causing all microbes to be excluded or killed, and a combination of the processings is possible.

Note that, in the description below, "upward" refers to a position further away from ground than a comparison target, and "downward" refers to a position closer to the ground than the comparison target. Further, "high" and "low" in the description below indicate a height relationship along a gravity direction.

The endoscope reprocessor 1 is provided with a controlling portion 5, a power source portion 6, a processing tank 2, a tank 20, a concentration meter 80, a first adjusting portion 91 and a second adjusting portion 92.

The controlling portion 5 can be configured being provided with an arithmetic device (CPU), a storage device (RAM), an auxiliary storage device, an input/output device, a power control device and the like, and has a configuration for controlling an operation of each portion constituting the endoscope reprocessor 1 based on a predetermined program. The controlling portion 5 includes a judging portion 5a configured to execute a judgment process to be described later and a maintaining portion 5b. The operation of each component included in the endoscope reprocessor 1 in the description below is controlled by the controlling portion 5 even if it is not especially described.

The power source portion 6 supplies power to each of the portions of the endoscope reprocessor 1. The power source portion 6 distributes power obtained from an outside such as a commercial power source to the respective portions. Note that the power source portion 6 may be provided with a power generation device or a battery.

The processing tank 2 is in a concave shape having an opening portion and is capable of storing liquid inside. An endoscope not shown can be arranged in the processing tank 2. In the present embodiment, a cover 3 configured to open and close the opening portion of the processing tank 2 is provided on a top portion of the processing tank 2, as an example. When reprocessing is performed for the endoscope in the processing tank 2, the opening portion of the processing tank 2 is closed by the cover 3.

The processing tank 2 is provided with a measurement target liquid nozzle 12, a drainage port 11, a circulation port 13, a circulation nozzle 14, a cleaning liquid nozzle 15, an endoscope connecting portion 16 and an accessories case 17.

The measurement target liquid nozzle 12 is an opening portion communicating with the tank 20 via a measurement target liquid conduit 26. The tank 20 stores measurement target liquid.

The measurement target liquid conduit 26 is provided with a measurement target liquid pump 27. By operating the measurement target liquid pump 27, the measurement target liquid in the tank 20 is transferred into the processing tank 2 via the measurement target liquid conduit 26 and the measurement target liquid nozzle 12.

In the tank 20, the concentration meter 80 configured to measure a concentration of the measurement target liquid 20 is attachably and detachably held by a holding portion 20b. A kind of the measurement target liquid stored in the tank 20 is not especially limited. In the present embodiment, the measurement target liquid is disinfecting liquid, for example, peracetic acid used for disinfecting processing, as an example. However, the present invention is not limited to the above, and cleaning liquid used for cleaning processing, highly volatile solution used for drying and the like can be appropriately selected as the measurement target liquid according to purposes.

Further, in the present embodiment, the measurement target liquid is such that is obtained by diluting undiluted solution of the measurement target liquid supplied from a measurement target liquid bottle 18 with water at a predetermined ratio, as an example. The tank 20 of the present embodiment communicates with a bottle connecting portion 19 configured to introduce the undiluted solution of the measurement target liquid supplied from the measurement target liquid bottle 18 into the tank 20 and a dilution conduit 48 configured to introduce water for dilution into the tank 20. By the measurement target liquid bottle 18 being connected to the bottle connecting portion 19, the undiluted solution of the measurement target liquid is introduced into the tank 20. A configuration for introducing water from the dilution conduit 48 into the tank 20 will be described later.

Note that the endoscope reprocessor 1 may not have the configuration for diluting the measurement target liquid with water or the like. Further, if the measurement target liquid is such that is obtained by mixing a plurality of kinds of undiluted solutions for use, the bottle connecting portion 19 can be connected to a plurality of measurement target liquid bottles 18.

Further, in the present embodiment, the measurement target liquid can be reused if the concentration is within a predetermined range in which efficacy is obtained, as an example. The tank 20 serves also as a measurement target liquid recovering portion 29 configured to recover the measurement target liquid transferred from the tank 20 into the processing tank 2 and re-store the measurement target liquid. In the description below, the tank 20 and the measurement target liquid recovering portion 29 will be merely referred to as the tank 20 when the tank 20 and the measurement target liquid recovering portion 29 are not distinguished from each other.

Note that the tank 20 may be provided separately from the measurement target liquid recovering portion 29. In the case of the configuration in which the tank 20 is different from the measurement target liquid recovering portion 29, a capacity of the tank 20 may be smaller than a capacity of the measurement target liquid recovering portion 29.

Further, a draining portion 28 may be arranged on the tank 20. The draining portion 28 discharges the measurement target liquid or liquid such as water from inside the tank 20. The draining portion 28 may be configured to discharge liquid from inside the tank 20 by gravity or may be configured to compulsorily discharge liquid from inside the tank 20 by a pump. Note that, as described later, in a case of discharging liquid in the tank 20 via other routes such as the measurement target liquid conduit 26, the tank 20 may not be provided with the draining portion 28.

In the present embodiment, the draining portion 28 includes a drain conduit 28a communicating with a drainage port 20a provided on or near a bottom face of the tank 20 and a drain valve 28b configured to open and close the drain conduit 28a, as an example. The drain valve 28b may be an electromagnetic on/off valve, opening/closing of which is controlled by the controlling portion 5, or may be a cock, opening/closing of which is performed by a user's manual operation.

Note that a route for discharging liquid from inside the tank 20 is not limited to the drain conduit. For example, by starting operation of the measurement target liquid pump 27, the liquid can be discharged from inside the tank 20 into the processing tank 2 via the measurement target liquid conduit 26 and the measurement target liquid nozzle 12.

In addition to the components described before, a water level sensor 55, the first pressurizing portion 91 and the second pressurizing portion 92 are arranged on the tank 20. The components will be described later.

The drainage port 11 is an opening portion provided at a lowest position in the processing tank 2. The drainage port 11 is connected to a discharge conduit 21. The discharge conduit 21 causes the drainage port 11 and a switching valve 22 to communicate with each other. A recovery conduit 23 and a disposal conduit 25 are connected to the switching valve 22. The switching valve 22 can switch among a state of the discharge conduit 21 being blocked, a state of the discharge conduit 21 and the recovery conduit 23 communicating with each other, and a state of the discharge conduit 21 and the disposal conduit 25 communicating with each other.

The recovery conduit 23 causes the tank 20 and the switching valve 22 to communicate with each other. Further, the disposal conduit 25 is provided with a discharge pump 24. The disposal conduit 25 is connected to drainage equipment for accepting liquid discharged from the endoscope reprocessor 1.

By causing the switching valve 22 to be in the closed state, liquid can be stored in the processing tank 2. Further, by causing the switching valve 22 to be in the state of the discharge conduit 21 and the recovery conduit 23 communicating with each other when the measurement target liquid is stored in the processing tank 2, the measurement target liquid is transferred from the processing tank 2 to the tank 20. Further, by causing the switching valve 22 to be in the state of the discharge conduit 21 and the disposal conduit 25 communicating with each other and staring operation of the discharge pump 24, the liquid in the processing tank 2 is sent out to the drainage equipment via the disposal conduit 25.

The circulation port 13 is an opening portion provided near a bottom face of the processing tank 2. The circulation port 13 communicates with a circulation conduit 13a. The circulation conduit 13a branches to two conduits, an endoscope circulation conduit 30 and a processing tank circulation conduit 40.

The endoscope circulation conduit 30 causes the circulation conduit 13a and a channel valve 32 to be described later to communicate with each other. The endoscope circulation conduit 30 is provided with a circulation pump 33. By operating, the circulation pump 33 transfers fluid in the endoscope circulation conduit 30 toward the channel valve 32.

In addition to the endoscope circulation conduit 30 described before, an intake conduit 34, an alcohol conduit 38 and a sending-out conduit 31 are connected to the channel valve 32. The channel valve 32 selectively causes any one conduit among the endoscope circulation conduit 30, the intake conduit 34 and the alcohol conduit 38 to communicate with the sending-out conduit 31.

One end portion of the intake conduit 34 is open in atmosphere, and the other end portion is connected to the channel valve 32. Note that one end portion of the intake conduit 34 is provided with a filter configured to filter gas which passes through, though it is not shown. An air pump 35 is provided in the intake conduit 34, and transfers gas in the intake conduit 34 toward the channel valve 32 by operating.

The alcohol conduit 38 causes an alcohol tank 37 configured to store alcohol and the channel valve 32 to communicate with each other. The alcohol stored in the alcohol tank 37 is, for example, ethanol. An alcohol concentration can be appropriately selected. An alcohol pump 39 is provided in the alcohol conduit 38, and transfers the alcohol in the alcohol tank 37 toward the channel valve 32 by operating.

By, when liquid is stored in the processing tank 2, causing the channel valve 32 to be in a state of the sending-out conduit 31 and the endoscope circulation conduit 30 communicating with each other and starting operation of the circulation pump 33, the liquid in the processing tank 2 is sent into the sending-out conduit 31 via the circulation port 13, the circulation conduit 13a and the endoscope circulation conduit 30.

Further, by causing the channel valve 32 to be in a state of the sending-out conduit 31 and the intake conduit 34 communicating with each other and starting operation of the air pump 35, air is sent into the sending-out conduit 31. Further, by causing the channel valve 32 to be in a state of the sending-out conduit 31 and the alcohol conduit 38 communicating with each other and starting operation of the alcohol pump 39, the alcohol in the alcohol tank 37 is sent into the sending-out conduit 31.

The sending-out conduit 31 branches to an endoscope connection conduit 31b and a case connection conduit 31c. The endoscope connection conduit 31b is connected to the endoscope connecting portion 16. Further, the case connection conduit 31c is connected to the accessories case 17.

Further, the sending-out conduit 31 is provided with a flow channel switching portion 31a. The flow channel switching portion 31a can switch into which of the endoscope connection conduit 31b and the case connection conduit 31c fluid sent from the channel valve 32 into the sending-out conduit 31 is to be caused to flow. Note that, at the time of switching, control may be performed so that a pressure on the endoscope connection conduit 31b side is constant.

The endoscope connecting portion 16 is connected to a pipe sleeve provided on an endoscope via an endoscope tube not shown. Further, the accessories case 17 is a basket-like member configured to accommodate accessories of the endoscope not shown. Therefore, fluid sent from the channel valve 32 into the sending-out conduit 31 is introduced into the pipe sleeve of the endoscope or into the accessories case 17.

The processing tank circulation conduit 40 causes the circulation conduit 13a and the circulation nozzle 14 to communicate with each other. The circulation nozzle 14 is an opening portion provided in the processing tank 2. The processing tank circulation conduit 40 is provided with a flow liquid pump 41.

Further, a three-way valve 42 is provided between the flow liquid pump 41 of the processing tank circulation conduit 40 and the circulation nozzle 14. A water supply conduit 43 is connected to the three-way valve 42. The three-way valve 42 can switch between a state of the circulation nozzle 14 and the processing tank circulation conduit 40 communicating with each other and a state of the circulation nozzle 14 and the water supply conduit 43 communicating with each other.

The water supply conduit 43 causes the three-way valve 42 and a water supply source connecting portion 46 to communicate with each other. The water supply conduit 43 is provided with a water introduction valve 45 configured to open/close the water supply conduit 43 and a water filter 44 configured to filter water. The water supply source connecting portion 46 is connected to a water supply source 49 such as waterworks sending out water, for example, via a hose.

A section of the water supply conduit 43 between the water filter 44 and the three-way valve 42 is provided with a dilution valve 47. The dilution conduit 48 causing the dilution valve 47 and the tank 20 to communicate with each other is connected to the dilution valve 47. The dilution valve 47 can switch between a state of the water filter 44 and the three-way valve 42 communicating with each other and a state of the water filter 44 and the dilution conduit 48 communicating with each other.

By, when liquid is stored in the processing tank 2, causing the three-way valve 42 to be in the state of the circulation nozzle 14 and the processing tank circulation conduit 40 communicating with each other, causing the dilution valve 47 to be in the state of the water filter 44 and the three-way valve 42 communicating with each other, and starting operation of the flow liquid pump 41, the liquid in the processing tank 2 is discharged from the circulation nozzle 14 via the circulation port 13, the circulation conduit 13a and the processing tank circulation conduit 40.

Further, by causing the three-way valve 42 to be in the state of the circulation nozzle 14 and the water supply conduit 43 communicating with each other, causing the dilution valve 47 to be in the state of the water filter 44 and the three-way valve 42 communicating with each other, and causing the water introduction valve 45 to be in an open state, water supplied from the water supply source 49 is discharged from the circulation nozzle 14. The liquid discharged from the circulation nozzle 14 is introduced into the processing tank 2.

Further, by causing the dilution valve 47 to be in the state of the water filter 44 and the dilution conduit 48 communicating with each other and causing the water introduction valve 45 in the open state, water supplied from the water supply source 49 is introduced into the tank 20.

The cleaning liquid nozzle 15 is an opening portion communicating with a cleaning liquid tank 50 storing cleaning liquid, via a cleaning liquid conduit 51. The cleaning liquid is used for cleaning processing. The cleaning liquid conduit 51 is provided with a cleaning liquid pump 52. By operating the cleaning liquid pump 52, cleaning liquid in the cleaning liquid tank 50 is transferred into the processing tank 2.

Further, the endoscope reprocessor 1 is provided with an operation portion 7 and an outputting portion 8 constituting a user interface configured to give and receive information to and from a user. The operation portion 7 and the outputting portion 8 are electrically connected to the controlling portion 5.

The operation portion 7 includes operation members, for example, push switches and a touch sensor. Further, the outputting portion 8 includes a display device configured to display, for example, an image and characters, a light emission device configured to emit light, a speaker configured to emit a sound, or a combination of these. Note that the operation portion 7 and the outputting portion 8 may be in a form of being provided in an electronic apparatus performing wireless communication with the controlling portion 5.

Figure 2:
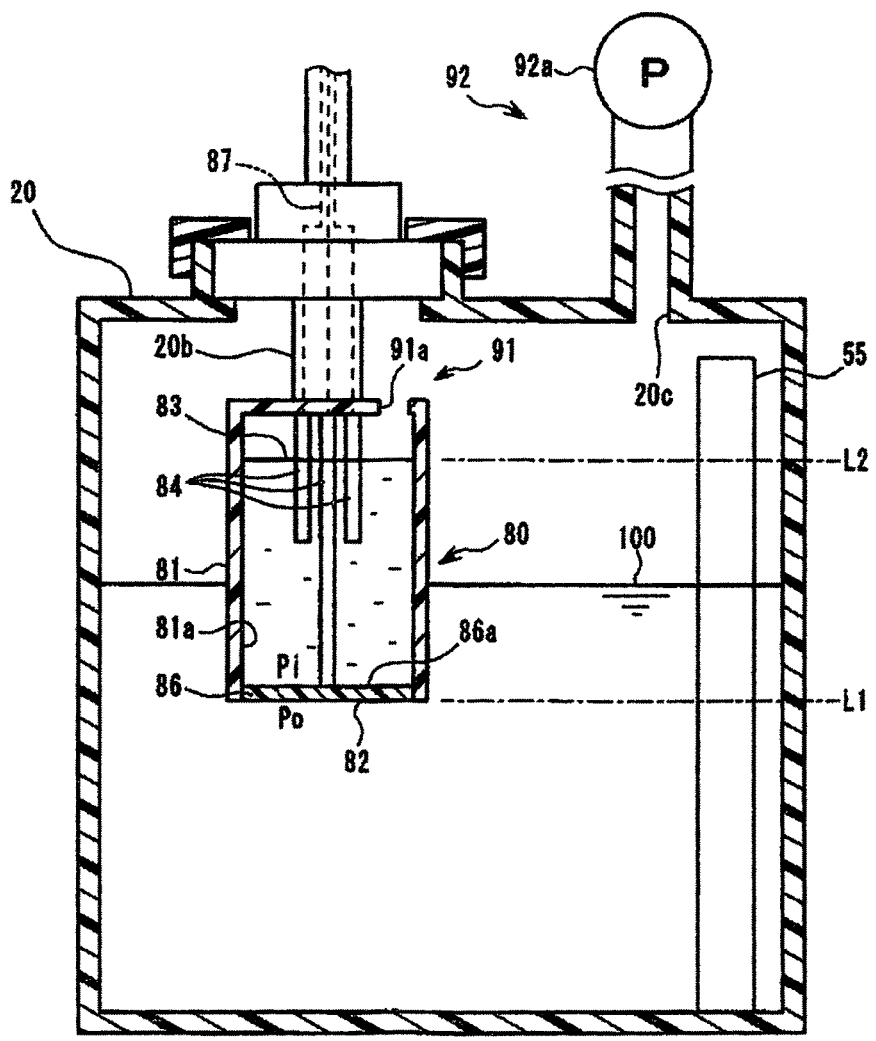
FIG. 2 is a cross-sectional view of a tank and a concentration meter of the first embodiment.

Next, a configuration of the tank 20 will be described. As shown in FIG. 2, the tank 20 is provided with the concentration meter 80, the water level sensor 55, the first adjusting portion 91 and the second adjusting portion 92. Further, a stirring mechanism configured to stir liquid may be provided in the tank 20 though the stirring mechanism is not shown.

The tank 20 can store the measurement target liquid up to a second water level L2 higher than a predetermined first water level L1. The tank 20 has a holding portion 20a configured to attachably and detachably hold the concentration meter 80 to be described later.

The concentration meter 80 measures a concentration of particular matter which is a measurement target in the measurement target liquid in contact with a measurement face 82. The concentration meter 80 may be in a form of being included in the endoscope reprocessor 1 and electrically connected to the controlling portion 5 or may be in a form of operating as a single body without being included in the endoscope reprocessor 1. In the present embodiment, the concentration meter 80 is electrically connected to the controlling portion 5 as an example, and information about a measurement result of a concentration of the measurement target liquid measured by the concentration meter 80 is inputted to the controlling portion 5.

The concentration meter 80 includes a housing 81, electrodes 84, an osmosis membrane 86 and internal liquid 83. The housing 81 is a container-shaped member provided with a hollow 81a.

The plurality of electrodes 84 are separately arranged inside the hollow 81a. The plurality of electrodes 84 are connected to a control device of the concentration meter 80 not shown via an electric cable 87. Note that the control device of the concentration meter 80 may be configured integrally with the housing 81. In the present embodiment, the control device of the concentration meter 80 is included in the controlling portion 5 as described before.

An opening portion of the hollow 81a is covered with the osmosis membrane 86. Further, the internal liquid 83 is stored inside the hollow 81a. An inner face 86a of the osmosis membrane 86 which is exposed to an inner side of the hollow 81a is in contact with the internal liquid 83. Further, in the hollow 81a, the plurality of electrodes 84 are submerged in the internal liquid 83.

The measurement face 82 of the concentration meter 80 is a face on an opposite side of the inner face 86a of the osmosis membrane 86. The osmosis membrane 86 causes measurement target matter in the measurement target liquid to pass through. Therefore, a concentration of the measurement target matter in the internal liquid 83 changes according to a concentration of the measurement target matter in the measurement target liquid which is in contact with the measurement face 82.

Figure 3:
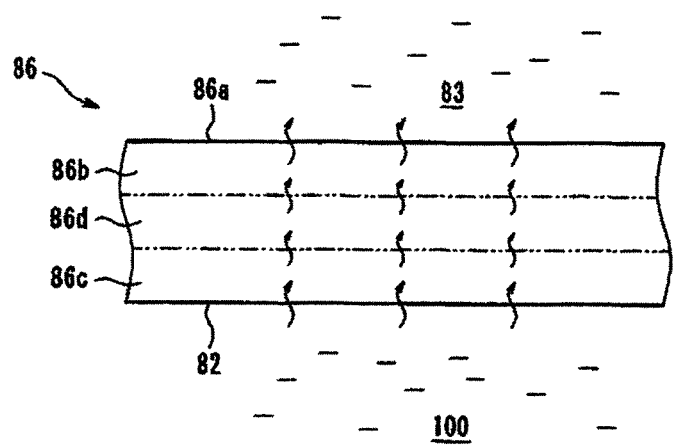
FIG. 3 is a diagram schematically showing a section of an osmosis membrane.

FIG. 3 is a diagram schematically showing that measurement target matter passes through the osmosis membrane 86. FIG. 3 shows a case where measurement target liquid 100 is in contact with the measurement face 82, and the measurement face 82 side of the osmosis membrane 86 is in a wet state. Further, in the state shown in FIG. 3, a concentration of the measurement target matter in the measurement target liquid 100 is higher than a concentration of the measurement target matter in the internal liquid 83.

The osmosis membrane 86 is a porous membrane which does not cause liquid molecules to pass through but causes gas molecules to pass through. On a section of the osmosis membrane 86 in a state of being arranged so as to separate the internal liquid 83 and the measurement target liquid 100 from each other, a first area 86b permeated with the internal liquid 83, a second area 86c permeated with the measurement target liquid 100, and a dry area 86d between the first area 86b and the second area 86c exist. Gas of the measurement target liquid 100 which has evaporated in the second area 86c of the osmosis membrane 86 passes through the dry area 86d and is dissolved into the internal liquid 83 in the first area 86b.

Since the internal liquid 83 is always stored in the hollow 81a, the internal liquid 83 continues to be in contact with the inner face 86a of the osmosis membrane 86, and, therefore, a thickness of the first area 86b is always substantially constant. The thickness of the first area 86b is a depth of permeation of the internal liquid 83 from the inner face 86a into the osmosis membrane 86. On the other hand, since the measurement target liquid 100 may be discharged from inside the tank 20, the measurement face 82 of the osmosis membrane 86 is not necessarily always in contact with liquid. Therefore, if the measurement face 82 continues to be exposed in air, an amount of moisture of the second area 86c gradually decreases. Then, if the measurement face 82 continues being exposed in air, the second area 86c disappears in the end, and the dry area 86d reaches the measurement face 82.

As described above, inside the hollow 81a of the housing 81 of the concentration meter 80, the internal liquid 83 is arranged between the electrodes 84 and the osmosis membrane 86, and the electrodes 84 and the osmosis membrane 86 are connected via the internal liquid 83. The term "connected" used here refers to a state in which measurement target matter which has passed through the osmosis membrane 86 and reaches an inside of the internal liquid 83 can reach the electrodes 84 with the internal liquid 83 as a medium.

The concentration meter 80 measures change in a potential difference which occurs among the plurality of electrodes 84 submerged in the internal liquid 83 or change in a value of a current which flows between paired electrodes 84, and measures the concentration of particular matter in the measurement target liquid in contact with the measurement face 82 based on a value of the measurement. Since a principal and configuration of such concentration measurement by the concentration meter 80 are well-known, detailed description will be omitted.

The holding portion 20*b* which the tank 20 has holds the concentration meter 80 so that the measurement face 82 of the osmosis membrane 86 of the concentration meter 80 is in contact with the measurement target liquid 100 inside the tank 20. The concentration meter 80 is held by the holding portion 20*b* being attachable to and detachable from the tank 20.

More specifically, the measurement face 82 of the concentration meter 80 held by the holding portion 20*b* is arranged at the predetermined first water level L1 in the tank 20. Note that a part of the concentration meter 80 in the state of being held by the holding portion 20*b* may be exposed outside the tank 20.

The water level sensor 55 detects a height of a surface of liquid stored in the tank 20. The water level sensor 55 is electrically connected to the controlling portion 5 and outputs information about a detection result to the controlling portion 5. In the present embodiment, the water level sensor 55 detects at least whether the liquid surface in the tank 20 has reached the first water level L1 or not, as an example.

Note that the water level sensor 55 may be used to, when undiluted solution of the measurement target liquid supplied from the measurement target liquid bottle 18 and water supplied from a dilution conduit are mixed in the tank 20, cause a volume ratio of the undiluted solution to the water to be a predetermined value.

The configuration of the water level sensor 55 is not especially limited. The water level sensor 55 may be, for example, a so-called electrode type water level sensor provided with a plurality of electrodes arranged separately from one another and configured to detect whether a liquid surface has reached a predetermined water level or not, based on whether electrical continuity among the plurality of electrodes, which changes according to whether the plurality of electrodes are submerged in liquid or not, exists or not. Further, the water level sensor 55 may be, for example, a so-called float type water level sensor configured to detect whether a liquid surface of the measurement target liquid has reached a predetermined water level or not based on an operation state of a switch configured to be opened or closed according to up and down motions of a float floating in the measurement target liquid.

The first adjusting portion 91 adjusts a pressure Pi of the internal liquid 83 of the concentration meter 80. A configuration of the first adjusting portion 91 for adjusting the pressure Pi of the internal liquid 83 is not especially limited. For example, the first adjusting portion 91 may be in a form of adjusting the pressure Pi of the internal liquid 83 by discharging gas in the hollow 81*a* of the housing 81 or sending air into the hollow 81*a*. Further, for example, the first adjusting portion 91 may be in a form of adjusting the pressure Pi of the internal liquid 83 by changing a capacity of the hollow 81*a*.

The second adjusting portion 92 adjusts a pressure Po of the measurement target liquid 100 stored in the tank 20. A configuration of the second adjusting portion 92 for adjusting the pressure Po of the measurement target liquid 100 is not especially limited. For example, the second adjusting portion 92 may be in a form of adjusting the pressure Po of the measurement target liquid 100 by discharging gas in the tank 20 or sending air into the tank 20. Further, for example, the second adjusting portion 92 may be in a form of adjusting the pressure Po of the measurement target liquid 100 by changing the capacity of the tank 20.

Further, one of the first adjusting portion 91 and the second adjusting portion 92 may be configured to passively adjust the pressure of the internal liquid 83 or the measurement target liquid 100 in response to an operation of the other. For example, if a ventilation portion through which gas comes and goes between an inside of the hollow 81*a* and an inside of the tank 20 is provided, it is possible to adjust both of the pressures Pi and Po of the internal liquid 83 and the measurement target liquid 100 by changing an air pressure of one of the hollow 81*a* and the tank 20.

Here, more particularly, the pressure Pi of the internal liquid 83 is a pressure of a part of the internal liquid 83 which is in contact with the inner face 86*a* of the osmosis membrane 86. Further, the pressure Po of the measurement target liquid 100 is a pressure of a part of the measurement target liquid 100 which is in contact with the measurement face 82 of the osmosis membrane 86.

In the present embodiment, the first adjusting portion 91 is provided with a ventilation portion 91*a* configured to cause gas to come and go between the inside of the hollow 81*a* and the inside of the tank 20, as an example. More particularly, the ventilation portion 91*a* is a hole passing through the housing 81. The ventilation portion 91*a* causes a part above the liquid surface of the internal liquid 83 in the hollow 81*a* and a part above the second water level L2 in the tank 20 to communicate with each other in the state in which the concentration meter 80 is held by the holding portion 20*b*. Note that the ventilation portion 91*a* may be provided with a porous membrane which causes gas to pass through but does not cause liquid to pass through. By the ventilation portion 91*a*, the air pressure inside the hollow 81*a* is equalized with the air pressure inside the tank 20.

The second adjusting portion 92 of the present embodiment adjusts the air pressure inside the tank 20. The second adjusting portion 92 is provided with a pump 92*a* capable of performing at least either discharge of gas from inside the tank 20 or sending-out of gas into the tank 20. The pump 92*a* is connected to a ventilation hole 20*c* provided above the second water level L2 in the tank 20.

In the present embodiment, the pump 92*a* discharges air in the tank 20 outside the tank 20 via the ventilation hole 20*c* by operating, as an example. The second adjusting portion 92 causes the pressure Po of the measurement target liquid 100 stored in the tank 20 to change by discharging the air in the tank 20 by the pump 92*a*. Then, since the first adjusting portion 91 of the present embodiment has a configuration for equalizing the air pressure inside the hollow 81*a* of the concentration meter 80 with the air pressure inside the tank 20, the first adjusting portion 91 passively adjusts the pressure Pi of the internal liquid 83 in response to an operation of the second adjusting portion 92.

Note that, on the contrary to the present embodiment, a form is also possible in which the first adjusting portion 91 is provided with a pump configured to discharge gas in the hollow 81*a*, and the second adjusting portion 92 is configured to equalize the air pressure inside the tank 20 with the air pressure inside the hollow 81*a*.

As described above, the endoscope reprocessor 1 of the present embodiment is provided with the first adjusting portion 91 and the second adjusting portion 92 configured to cause the pressure Pi of the internal liquid 83 of the concentration meter 80 and the pressure Po of the measurement target liquid 100 stored in the tank 20 in which the concentration meter 80 is arranged to change.

The operation of adjusting the pressures of the internal liquid 83 and the measurement target liquid 100 by the first adjusting portion 91 and the second adjusting portion 92 is controlled by the controlling portion 5.

The controlling portion 5 controls the first adjusting portion 91 and the second adjusting portion 92 so that a first state in which the pressure Pi of the internal liquid 83 is a first pressure P1, and the pressure Po of the measurement target liquid 100 is a second pressure P2, and a second state in which the pressure Pi of the internal liquid 83 is a third pressure P3 lower than the first pressure P1, and the pressure Po of the measurement target liquid 100 is a fourth pressure P4 lower than the second pressure P2 occur in the endoscope reprocessor 1. Further, the controlling portion 5 controls the first adjusting portion 91 and the second adjusting portion 92 so that the pressure Pi of the internal liquid 83 and the pressure Po of the measurement target liquid 100 are almost equal to each other.

Since the first adjusting portion 91 only performs the passive operation in the present embodiment as described before, the controlling portion 5 of the present embodiment controls the operation of the second adjusting portion 92 to cause the pressure Po of the measurement target liquid 100 in the tank 20 to change to the second pressure P2 or the fourth pressure P4. Then, in the present embodiment, when the pressure Po of the measurement target liquid 100 is adjusted to the second pressure P2 by the second adjusting portion 92, the pressure Pi of the internal liquid 83 is adjusted to the first pressure P1. Further, when the pressure Po of the measurement target liquid 100 is adjusted to the second pressure P2 by the second adjusting portion 92, the pressure Pi of the internal liquid 83 is adjusted to the first pressure P1.

In the present embodiment, the pressure Pi of the internal liquid 83 and the pressure Po of the measurement target liquid 100 are almost equal to each other. By equalizing the pressure Pi of the internal liquid 83 and the pressure Po of the measurement target liquid 100 with each other, it is possible to prevent deterioration of the osmosis membrane 86 due to the osmosis membrane 86 being deformed by change in the pressure Pi of the internal liquid 83 and the pressure Po of the measurement target liquid 100.

More specifically, in the present embodiment, the controlling portion 5 generates the first state by causing the pump 92a of the second adjusting portion 92 to enter a stop state. That is, in the first state of the present embodiment, the air pressures inside the tank 20 and the hollow 81a are atmospheric pressure, and the pressure Pi of the internal liquid 83 and the pressure Po of the measurement target liquid 100 are the first pressure P1 and the second pressure P3 based on the atmospheric pressure.

Further, in the present embodiment, the controlling portion 5 generates the second state by causing the pump 92a of the second adjusting portion 92 to operate. That is, in the second state of the present embodiment, the air pressures inside the tank 20 and the hollow 81a are a predetermined value lower than the atmospheric pressure, and the pressure Pi of the internal liquid 83 and the pressure Po of the measurement target liquid 100 are the third pressure P3 and the fourth pressure P4 based on the value.

The endoscope reprocessor 1 of the present embodiment is provided with the maintaining portion 5b configured to maintain the second state for a predetermined time period. The maintaining portion 5b may be included in the controlling portion 5 as in FIG. 1, or may be a separate body configured to act on the first adjusting portion, the second adjusting portion or the controlling portion 5 so that the controlling portion 5 maintains the second state.

The predetermined time period stated here is not especially limited but may be any time period in which predetermined matter permeates in the osmosis membrane 86 and concentration measurement is enabled, and preferably is five seconds or more. Note that the maintaining portion 5b may continually or intermittently adjust air pressure within the predetermined time period.

A reduced pressure state which instantaneously occurs "at time of an on/off operation of a power source" or "at time of a pulsatory motion of a pump" which generally occurs for a period shorter than one second is not included in the case of maintaining the second state in the present embodiment.

Next, an operation of the endoscope reprocessor 1 will be described.

The controlling portion 5 executes concentration measurement of the measurement target liquid 100 by the concentration meter 80 when it has been detected by the water level sensor 55 that the measurement target liquid 100 is stored above the first water level L1 in the tank 20. That is, the concentration measurement operation is executed when the measurement target liquid 100 is in contact with the measurement face 82 of the osmosis membrane 86 of the concentration meter 80.

Figure 4:
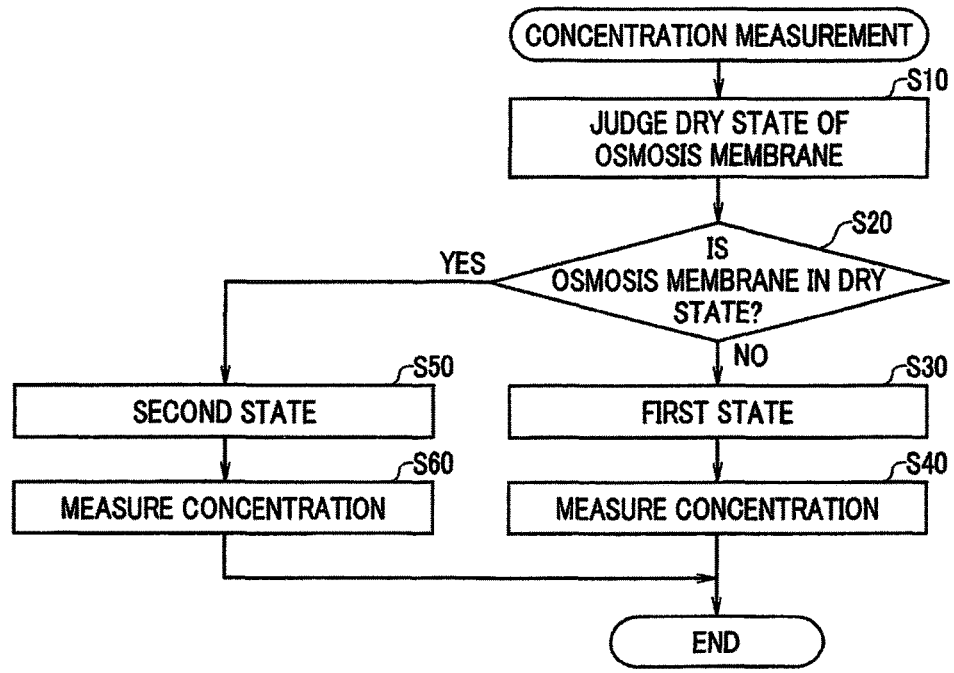
FIG. 4 is a flowchart of a concentration measurement operation of the endoscope reprocessor of the first embodiment.

FIG. 4 is a flowchart of the concentration measurement operation of the endoscope reprocessor 1. As shown in FIG. 4, in the concentration measurement operation, the controlling portion 5 judges whether the osmosis membrane 86 is in a dry state or not by the judging portion 5a at step S10 first. Here, the dry state refers to a case where the amount of moisture in the second area 86c of the section of the osmosis membrane 86 is equal to or smaller than a predetermined value or a case where the second area 86c does not exist on the section of the osmosis membrane 86, and the dry area 86d has reached the measurement face 82.

Further, the "judgment" by the judging portion 5a stated here is a process performed based on a value of some variable on a program executed by the controlling portion 5 and is not limited to a form of directly recognizing the dry state of the osmosis membrane 86 by a sensor or the like provided in the endoscope reprocessor. For example, at step S10, the controlling portion 5 may presume whether the osmosis membrane 86 is in the dry state or not based on stored information of past operation dates of the endoscope reprocessor and cause the presumption to be a judgment result. Further, for example, at step S10, the controlling portion 5 may judge whether the osmosis membrane 86 is in the dry state or not based on information inputted to the operation portion 7 by the user.

In the present embodiment, at step S10, the controlling portion 5 judges that the osmosis membrane 86 is in the dry state when the concentration measurement operation is concentration measurement operation executed for the first time after operation of diluting the measurement target liquid 100 is executed in the tank 20, as an example. The operation of diluting the measurement target liquid 100 is an operation of mixing undiluted solution of unused measurement target liquid and water in the tank 20 at a predetermined ratio after discharging used measurement target liquid 100 in the endoscope reprocessor 1 outside the apparatus.

Note that a process of the controlling portion 5 judging that the osmosis membrane 86 is in the dry state when the concentration measurement operation being executed is such that is executed for the first time after the measurement face 82 of the concentration meter 80 is continuously exposed in air for a predetermined time period or more may be added to step S10. The period during which the measurement face 82 is exposed in air includes a period of a state in which used measurement target liquid 100 in the endoscope reprocessor 1 has been discharged outside the apparatus. In this case, if it is detected by the water level sensor 55 that a state in which the liquid surface in the tank 20 is lower than the first water level L1 has continued for the predetermined time period or more, the controlling portion 5 judges that the osmosis membrane 86 is in the dry state.

If it is judged at step S10 that the osmosis membrane 86 is not in the dry state (step S20: NO), the flow proceeds to step S30. That is, if it is judged that the amount of moisture of the second area 86c of the osmosis membrane 86 exceeds the predetermined value, and the measurement face 82 is in the wet state, the flow proceeds to step S30.

At step S30, the controlling portion 5 controls the first adjusting portion 91 and the second adjusting portion 92 to generate the first state in which the pressure Pi of the internal liquid 83 is the first pressure P1, and the pressure Po of the measurement target liquid 100 is the second pressure P2. As described before, in the present embodiment, the controlling portion 5 generates the first state by causing the pump 92a of the second adjusting portion 92 to enter the stop state.

Then, at step S40, the controlling portion 5 controls the concentration meter 80 to execute concentration measurement of the measurement target liquid 100.

On the other hand, if it is judged at step S10 that the osmosis membrane 86 is in the dry state (step S20: YES), the flow proceeds to step S50. That is, if it is judged that the amount of moisture in the second area 86c of the osmosis membrane 86 is equal to or smaller than the predetermined value, the flow proceeds to step S50.

At step S50, the controlling portion 5 controls the first adjusting portion 91 and the second adjusting portion 92 to generate the second state in which the pressure Pi of the internal liquid 83 is the third pressure P3, and the pressure Po of the measurement target liquid 100 is the fourth pressure P4. As described before, in the present embodiment, the controlling portion 5 generates the second state by causing the pump 92a of the second adjusting portion 92 to operate. Further, as described before, the second state is maintained by the maintaining portion 5b for the predetermined time period.

Then, at step S60, the controlling portion 5 controls the concentration meter 80 to execute concentration measurement of the measurement target liquid 100.

In the concentration measurement operation described above, the pressure (P4) of the measurement target liquid 100 in the second state is lower than the pressure (P3) of the measurement target liquid 100 in the first state. Therefore, the measurement target liquid 100 in the second state is in a state of being easily evaporated in comparison with the measurement target liquid 100 in the first state. Therefore, an amount of evaporation of the measurement target liquid 100 in the second area 86c of the osmosis membrane 86 increases in the second state more than in the first state.

By the amount of evaporation of the measurement target liquid 100 in the second area 86c of the osmosis membrane 86 increasing, an amount of the measurement target matter which passes through the osmosis membrane 86 from the measurement target liquid 100 in contact with the measurement face 82 and reaches the internal liquid 83 increases.

Further, in the present embodiment, not only the pressure Po of the measurement target liquid 100 but also the pressure Pi of the internal liquid 83 is lower in the second state than in the first state. Thereby, steam of the measurement target liquid 100 passing through the dry area 86d of the osmosis membrane 86 and permeating into the internal liquid 83 in the first area 86b is caused to be accelerated.

Thus, in the second state, it is possible to increase the amount of the measurement target matter which passes through the osmosis membrane 86 from the measurement target liquid 100 in contact with the measurement face 82 and reaches the internal liquid 83 in comparison with the first state. If the amount of the measurement target matter which passes through the osmosis membrane 86 increases, a response speed of matter concentration in the internal liquid 83, which changes according to a concentration of particular measurement target matter in the measurement target liquid 100, can be increased.

As described above, at the time of executing the concentration measurement operation when the osmosis membrane 86 of the concentration meter 80 is in the dry state, the endoscope reprocessor 1 of the present embodiment increases the amount of the measurement target matter which passes through the osmosis membrane 86 by generating the second state and maintaining the second state for the predetermined time period, and, thereby, the endoscope reprocessor 1 can execute concentration measurement of the measurement target liquid 100 by the concentration meter 80 without delay even if the osmosis membrane 86 is in the dry state.

Therefore, even in a case where the measurement target liquid 100 does not exist in the tank 20, and the osmosis membrane 86 is in the dry state, for example, like a case where the measurement target liquid 100 is discharged from inside the tank 20 on a weekend, and new unused measurement target liquid is supplied into the tank 20 on a weekday, the endoscope reprocessor 1 of the present embodiment can execute concentration measurement of the measurement target liquid 100 by the concentration meter 80 without delay after supplying the measurement target liquid 100 into the tank 20 and start succeeding reprocessing.

Note that, though the air pressures inside the tank 20 and the hollow 81a are assumed to be the atmospheric pressure in the first state, and the air pressures inside the tank 20 and the hollow 81a are set to be lower than the atmospheric pressure in the second state in the present embodiment, the present invention is not limited to this.

For example, such a case is also included in the present invention that the pump 92a is configured to send air into the tank 20 when being operated, and the air pressures inside the tank 20 and the hollow 81a are caused to be higher than the atmospheric pressure by operating the pump 92a in the first state and caused to be the atmospheric pressure by stopping the pump 92a in the second state. In such a modification also, since the amount of the measurement target matter which passes through the osmosis membrane 86 in the second state increases more than in the first state, it is possible to execute concentration measurement of the measurement target liquid 100 by the concentration meter 80 without delay even if the osmosis membrane 86 is in the dry state, similarly to the embodiment described before.

Second Embodiment

Next, a second embodiment of the present invention will be described. Only points different from the first embodiment will be described below. Components similar to the components of the first embodiment will be given same reference numerals, and description of the components will be appropriately omitted.

Figure 5:
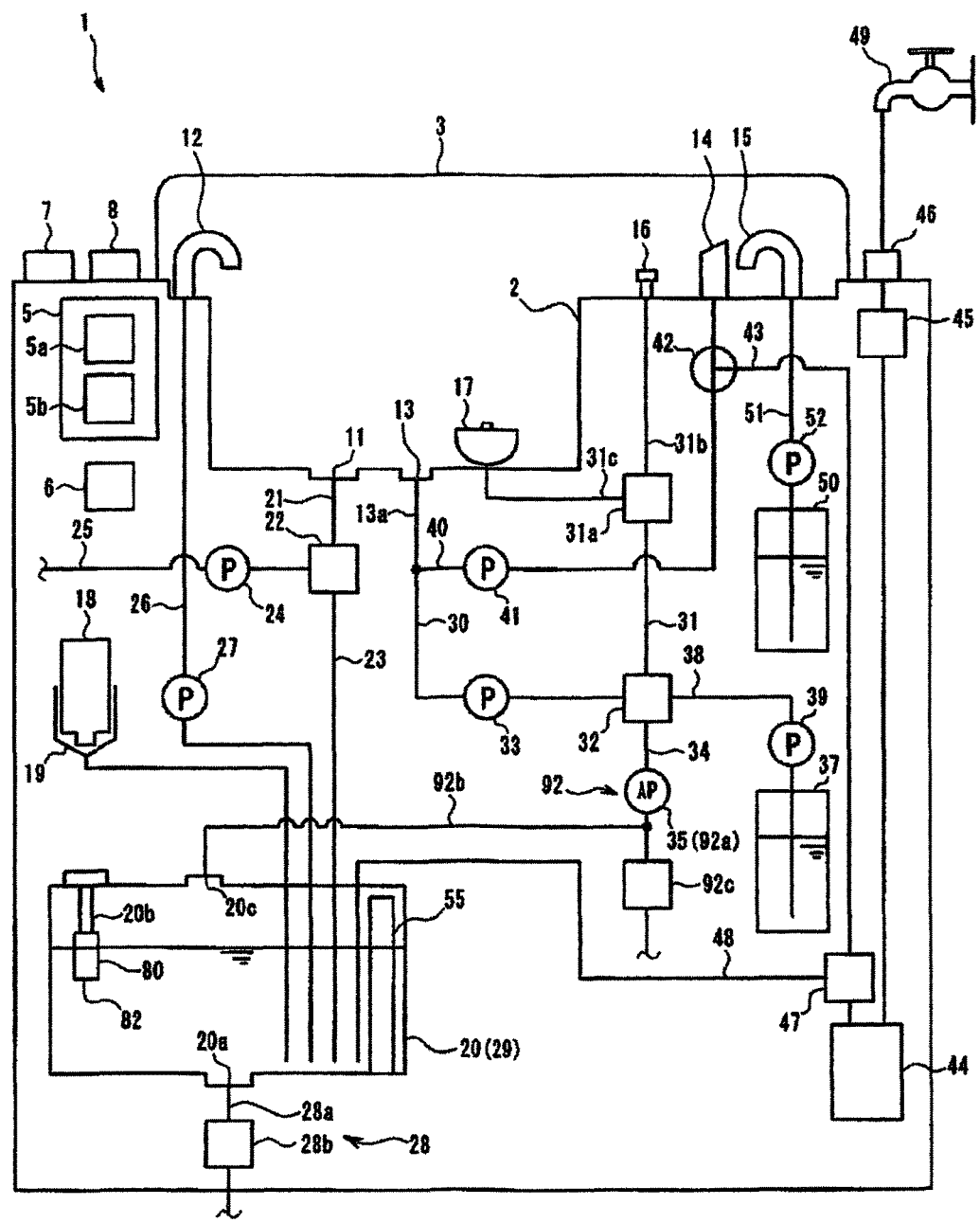
FIG. 5 is a diagram showing a configuration of an endoscope reprocessor of a second embodiment.

FIG. 5 is a diagram showing a configuration of the endoscope reprocessor 1 of the present embodiment. In the present embodiment, the configuration of the second adjusting portion 92 configured to adjust the pressure Po of the measurement target liquid 100 stored in the tank 20 is different from the first embodiment.

As shown in FIG. 5, the pump 92a of the second adjusting portion 92 of the present embodiment serves also as the air pump 35. The pump 92a is connected to the ventilation hole 20c of the tank 20 via a draft conduit 92b. The draft conduit 92b is provided with an open valve 92c which is an electromagnetic valve. The open valve 92c leaves an inside of the draft conduit 92b open in the atmospheric pressure when the open valve 92c is in an open state.

In the present embodiment, in a case of discharging air from inside the tank 20, operation of the pump 92a is started after causing the open valve 92c to be in a closed state and causing the channel valve 32 to be in the state of the sending-out conduit 31 and the intake conduit 34 communicating with each other. In this case, air in the tank 20 is discharged outside the tank 20 by the pump 92a operating.

Further, in the present embodiment, in a case of sending air into the endoscope connection conduit 31b or the case connection conduit 31c at the time of executing reprocessing, operation of the pump 92a is started after causing the open valve 92c to be in the open state and causing the channel valve 32 to be in the state of the sending-out conduit 31 and the intake conduit 34 communicating with each other. In this case, by the pump 92a operating, air caused to flow into the draft conduit 92b from the open valve 92c is sent into the endoscope connection conduit 31b or the case connection conduit 31c.

The concentration measurement operation by the endoscope reprocessor 1 of the present embodiment is similar to the concentration measurement operation of the first embodiment. Therefore, similarly to the first embodiment, at the time of executing the concentration measurement operation when the osmosis membrane 86 of the concentration meter 80 is in the dry state, the endoscope reprocessor 1 of the present embodiment increases the amount of the measurement target matter which passes through the osmosis membrane 86 by generating the second state and, thereby, can execute concentration measurement of the measurement target liquid 100 by the concentration meter 80 without delay even if the osmosis membrane 86 is in the dry state.

Third Embodiment

Next, a third embodiment of the present invention will be described. Only points different from the first and second embodiments will be described below. Components similar to the components of the first and second embodiments will be given same reference numerals, and description of the components will be appropriately omitted.

Figure 6:
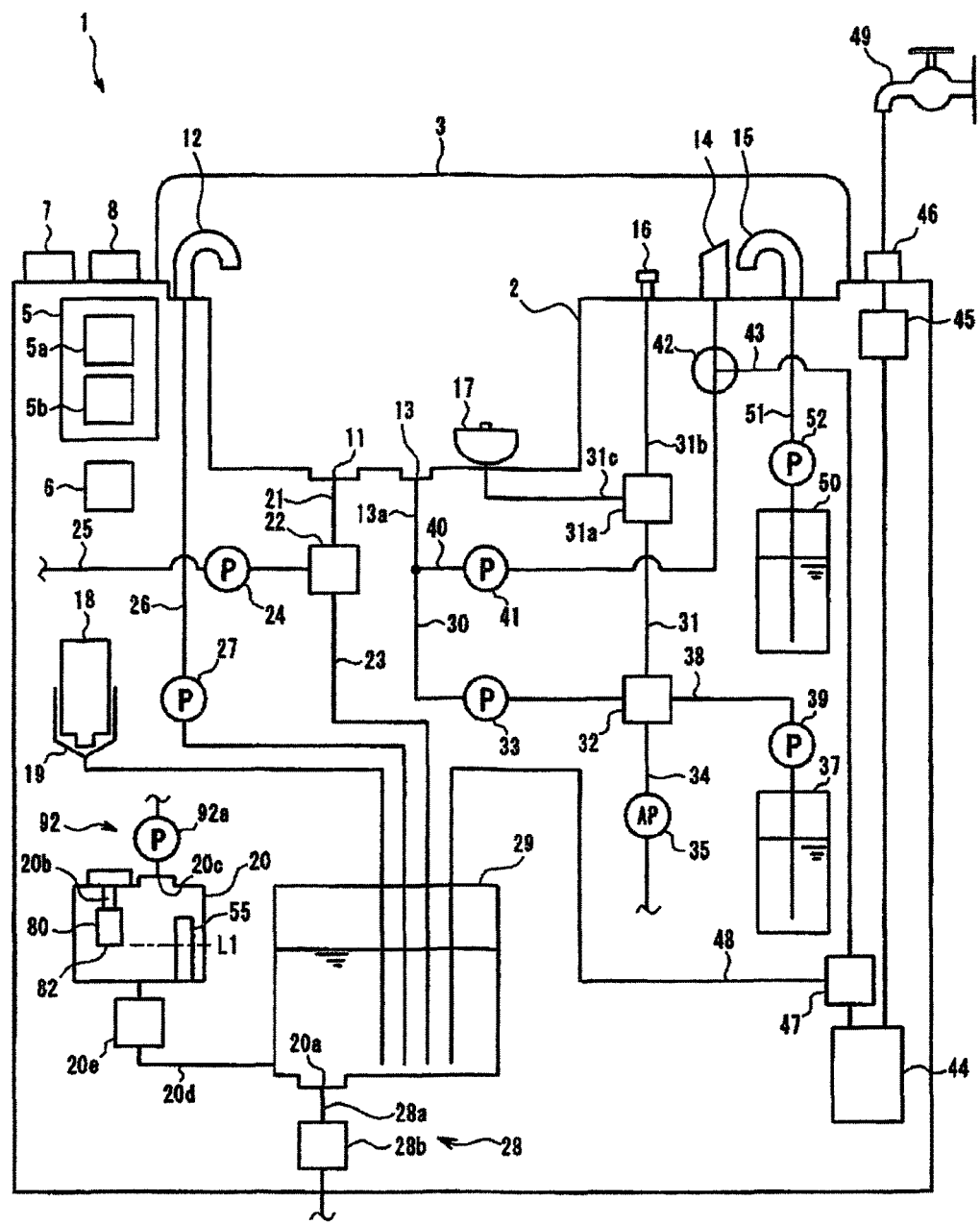
FIG. 6 is a diagram showing a configuration of an endoscope reprocessor of a third embodiment.

FIG. 6 is a diagram showing a configuration of the endoscope reprocessor 1 of the present embodiment. The present embodiment is different from the first and second embodiments in a point that the tank 20 in which the concentration meter 80 is arranged and the measurement target liquid recovering portion 29 are provided as different containers.

The measurement target liquid recovering portion 29 stores the measurement target liquid 100 more than a minimum amount required for execution of reprocessing by the endoscope reprocessor 1. The measurement target liquid recovering portion 29 communicates with the bottle connecting portion 19, the recovery conduit 23, the medicinal solution conduit 26, the dilution conduit 48 and the drain conduit 28a. The drain conduit 28a communicates with the drainage port 20a provided on or near a bottom face of the measurement target liquid recovering portion 29. Configurations of the conduits are similar to the first and second embodiments described before.

The tank 20 of the present embodiment communicates with the measurement target liquid recovering portion 29 via a supply conduit 20d. The supply conduit 20d is provided with an opening/closing valve 20e which is an electromagnetic valve configured to open and close the supply conduit 20d.

Similarly to the first embodiment, the tank 20 is provided with the concentration meter 80, the water level sensor 55, the first adjusting portion 91 and the second adjusting portion 92. Since configurations of the above are similar to the first and second embodiments, description of the configurations will be omitted.

In the present embodiment, when the opening/closing valve 20e is in an open state, the water level of the measurement target liquid 100 stored in the tank 20 changes according to change in the water level of the measurement target liquid 100 stored in the measurement target liquid recovering portion 29.

In the present embodiment, in the case of causing the air pressure inside the tank 20 to change, operation of the pump 92a is started after causing the opening/closing valve 20e to be in a closed state.

The concentration measurement operation by the endoscope reprocessor 1 of the present embodiment is almost similar to the first embodiment but is different from the first embodiment in the point that, in the case of controlling the second adjusting portion 92 to cause the air pressure inside the tank 20 to change, the opening/closing valve 20e is caused to be in the closed state as described before.

Similarly to the first and second embodiments, at the time of executing the concentration measurement operation when the osmosis membrane 86 of the concentration meter 80 is in the dry state, the endoscope reprocessor 1 of the present embodiment increases the amount of the measurement target matter which passes through the osmosis membrane 86 by generating the second state, and, thereby, can execute concentration measurement of the measurement target liquid 100 by the concentration meter 80 without delay even if the osmosis membrane 86 is in the dry state.

Fourth Embodiment

Next, a fourth embodiment of the present invention will be described. Only points different from the first to third embodiments will be described below. Components similar to the first to third embodiments will be given same reference numerals, and description of the components will be appropriately omitted.

Figure 7:
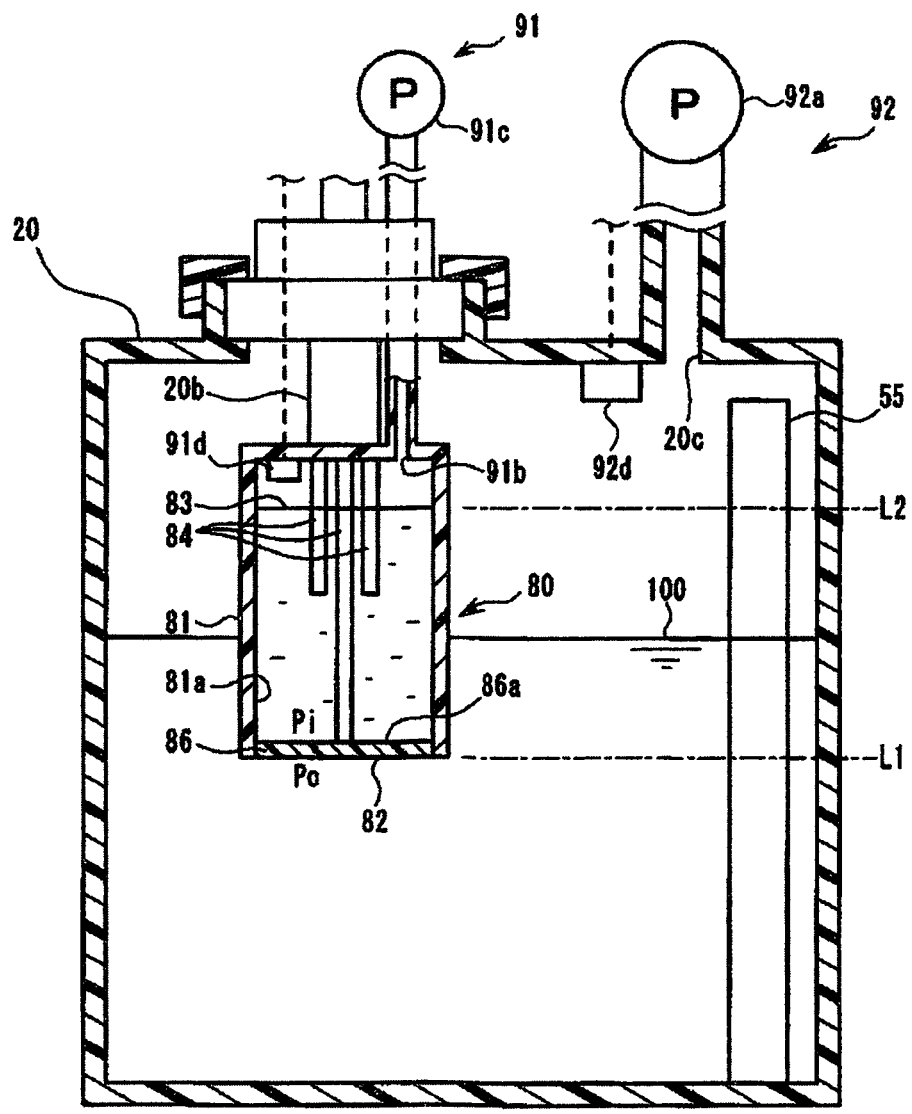
FIG. 7 is a diagram showing a configuration of a first adjusting portion and a second adjusting portion of a fourth embodiment.

The endoscope reprocessor 1 of the present embodiment is different from the first to third embodiments in the configuration of the first adjusting portion 91 and the second adjusting portion 92. FIG. 7 is a diagram showing the configuration of the first adjusting portion 91 and the second adjusting portion 92 of the present embodiment.

As shown in FIG. 7, the first adjusting portion 91 of the present embodiment is provided with a pump 91c capable of at least one of discharge of gas from inside the hollow 81a of the concentration meter 80 and sending-out of gas into the hollow 81a. The pump 91c is connected to a ventilation hole 91c provided in the hollow 81a. The ventilation hole 91c is provided above the liquid surface of the internal liquid 83 stored in the hollow 81a.

Further, the first adjusting portion 91 is provided with a first air pressure measuring portion 91d configured to measure the air pressure inside the hollow 81a. The first air pressure measuring portion 91d is connected to the controlling portion 5. Information about the air pressure inside the hollow 81a measured by the first air pressure measuring portion 91d is inputted to the controlling portion 5.

The operation of the first adjusting portion 91 is controlled by the controlling portion 5. In the present embodiment, the pump 91c discharges air in the hollow 81a outside the hollow 81a and the tank 20 via the ventilation hole 91b by operating, as an example. The first adjusting portion 91 causes the pressure Pi of the internal liquid 83 stored in the hollow 81a to change by discharging the air in the hollow 81a by the pump 91c.

The second adjusting portion 92 of the present embodiment adjusts the air pressure inside the tank 20. The second adjusting portion 92 is provided with the pump 92a capable of performing at least one of discharge of gas from inside the tank 20 and sending-out of gas into the tank 20. The pump 92a is connected to the ventilation hole 20c provided above the second water level L2 in the tank 20.

Further, the second adjusting portion 92 is provided with a second air pressure measuring portion 92d configured to measure the air pressure inside the tank 20. The second air pressure measuring portion 92d is connected to the controlling portion 5. Information about the air pressure inside the tank 20 measured by the second air pressure measuring portion 92d is inputted to the controlling portion 5.

The operation of the second adjusting portion 92 is controlled by the controlling portion 5. In the present embodiment, the pump 92a discharges air in the tank 20 outside the tank 20 via the ventilation hole 20c by operating, as an example. The second adjusting portion 92 causes the pressure Po of the measurement target liquid 100 stored in the tank 20 to change by discharging air in the tank 20 by the pump 92a.

In the present embodiment, the generation of the first state at step S30 of the concentration measurement operation shown in FIG. 4 is performed by the controlling portion 5 causing the pump 91c of the first adjusting portion 91 and the pump 92a of the second adjusting portion 92 to enter the stop state. By causing the pump 91c of the first adjusting portion 91 and the pump 92a of the second adjusting portion 92 to be in the stop state, the air pressures inside the hollow 81a and the air pressure in the tank 10 become the atmospheric pressure, the pressure Pi of the internal liquid 83 becomes the first pressure P1, and the pressure Po of the measurement target liquid 100 becomes the second pressure P2.

Further, at step S50 of the concentration measurement operation shown in FIG. 4, the controlling portion 5 operates the pump 91c and the pump 92a based on measurement results of the first air pressure measuring portion 91d and the second air pressure measuring portion 92d so that the air pressure inside the hollow 81a and the air pressure inside the tank 10 equally become a predetermined air pressure lower than the atmospheric pressure. Thereby, the pressure Pi of the internal liquid 83 becomes the third pressure P3, and the pressure Po of the measurement target liquid 100 becomes the fourth pressure P4.

Other components and operations of the endoscope reprocessor 1 are similar to the first embodiment. Therefore, as described in the first embodiment, at the time of executing the concentration measurement operation when the osmosis membrane 86 of the concentration meter 80 is in the dry state, the endoscope reprocessor 1 of the present embodiment increases the amount of the measurement target matter which passes through the osmosis membrane 86 by generating the second state and, thereby, can execute concentration measurement of the measurement target liquid 100 by the concentration meter 80 without delay even if the osmosis membrane 86 is in the dry state.

Note that, as in the second embodiment, one of the pump 91c of the first adjusting portion 91 and the pump 92a of the second adjusting portion 92 of the present embodiment may serve also as the air pump 35. Further, as in the third embodiment, the tank 20 may be provided as a container different from the measurement target liquid recovering portion 29.

Fifth Embodiment

Next, a fifth embodiment of the present invention will be described. Only points different from the first to fourth embodiments will be described below. Components similar to the components of the first to fourth embodiments will be given same reference numerals, and description of the components will be appropriately omitted.

In the first to fourth embodiments described before, the first adjusting portion 91 and the second adjusting portion 92 have a configuration in which the pressure Pi of the internal liquid 83 and the pressure Po of the measurement target liquid 100 are adjusted by causing the air pressures inside the hollow 81a and the tank 20 to change by the pumps. On the other hand, the first adjusting portion 91 and the second adjusting portion 92 of the present embodiment adjust the pressure Pi of the internal liquid 83 and the pressure Po of the measurement target liquid 100 by causing capacities of the hollow 81a and the tank 20 to change.

Figure 8:
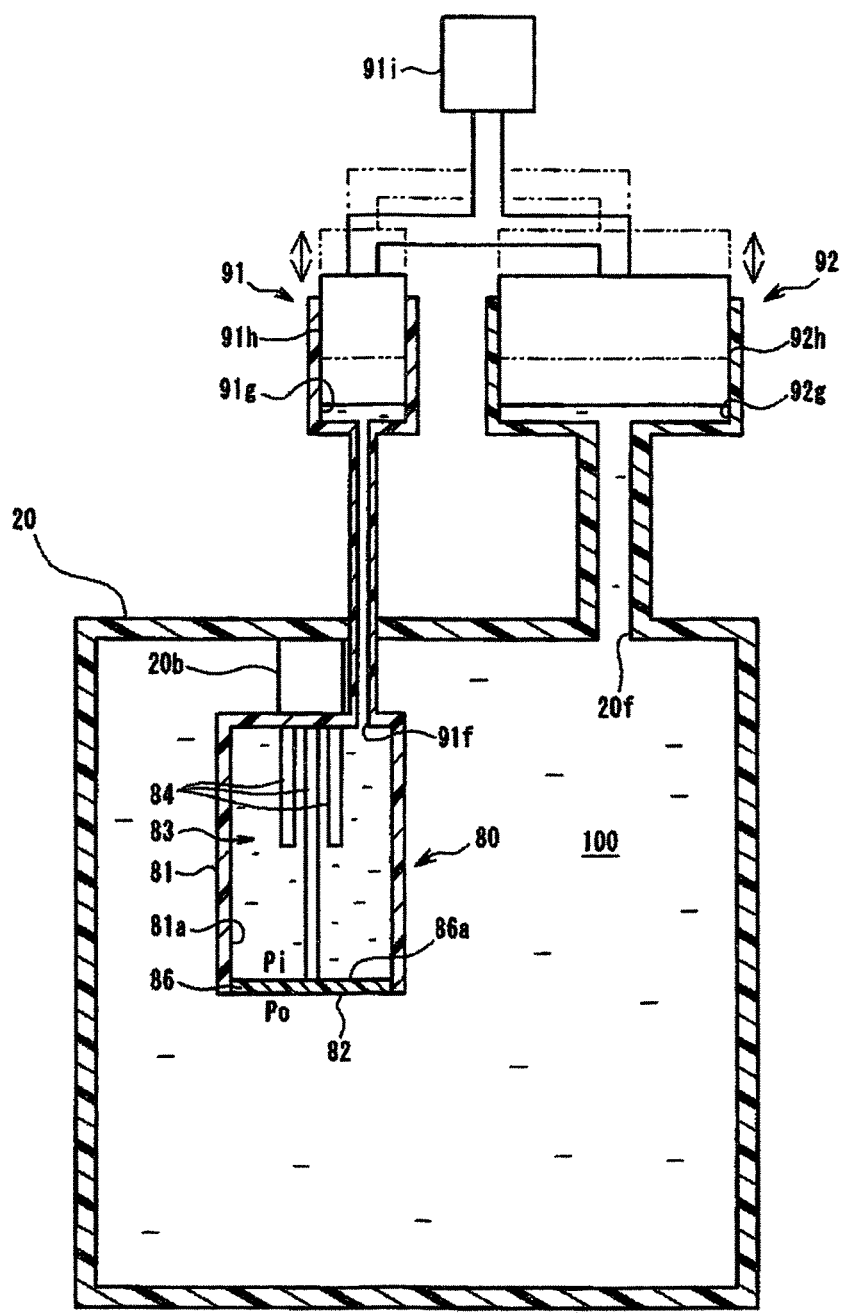
FIG. 8 is a diagram showing a configuration of a first adjusting portion and a second adjusting portion of a fifth embodiment.

FIG. 8 is a diagram showing the configuration of the first adjusting portion 91 and the second adjusting portion 92 of the present embodiment. As shown in FIG. 8, the first adjusting portion 91 is provided with a first cylinder 91g communicating with the inside of the hollow 81a of the concentration meter 80, a first piston 91h configured to slide in the first cylinder 91g, and an actuator 91i configured to drive the first piston 91h.

The first cylinder 91g communicates with the inside of the hollow 81a via a communicating hole 91f which opens in the hollow 81a. That is, the capacity of the hollow 81a includes a capacity of the first cylinder 91g.

The capacity of an inside of the first cylinder 91g changes by movement of the first piston 91h. Therefore, the first adjusting portion 91 of the present embodiment causes the first piston 91h to move by the actuator 91i to cause the capacity of the hollow 81a to change, and, thereby, adjusts the pressure Pi of the internal liquid 83.

The second adjusting portion 92 is provided with a second cylinder 92g communicating with a communicating hole 20f which opens in the tank 20 and a second piston 92h configured to slide in the second cylinder 92g. In the present embodiment, the second cylinder 92g is driven by the actuator 91i so as to move with a same amount of stroke as the first cylinder 91h.

Since the second cylinder 92g communicates with the inside of the tank 20, the capacity of the tank 20 includes a capacity of the second cylinder 92g. The capacity of the second cylinder 92g changes by movement of the second piston 92h. Therefore, the second adjusting portion 92 of the present embodiment causes the second piston 92h to move by the actuator 91i to cause the capacity of the tank 20 to change, and, thereby, adjusts the pressure Po of the measurement target liquid 100.

In the present embodiment, a ratio of an area of the second piston 92h to an area of the first piston 91h is in proportion to a ratio of the capacity of the tank 20 to the capacity of the hollow 81a. Therefore, if the first piston 91h and the second piston 92h are caused to move with the same amount of stroke, the pressure Pi of the internal liquid 83 and the pressure Po of the measurement target liquid 100 increase or decrease while keeping a relationship of equality.

In the present embodiment, the generation of the first state at step S30 of the concentration measurement operation shown in FIG. 4 is performed by driving the first piston 91h and the second piston 92h by the actuator 91i to cause the capacities of the first cylinder 91g and the second cylinder 92g to be predetermined first and second capacities. Thereby, the pressure Pi of the internal liquid 83 becomes the first pressure P1, and the pressure Po of the measurement target liquid 100 becomes the second pressure P2.

Further, the generation of the second state at step S50 of the concentration measurement operation shown in FIG. 4 is performed by driving the first piston 91h and the second piston 92h by the actuator 91i to cause the capacities of the first cylinder 91g and the second cylinder 92g to be predetermined third and fourth capacities. Here, the third and fourth capacities are larger than the first and second capacities described before. Thereby, the pressure Pi of the internal liquid 83 becomes the third pressure P3, and the pressure Po of the measurement target liquid 100 becomes the fourth pressure P4.

Other components and operations of the endoscope reprocessor 1 are similar to the first embodiment. Therefore, as described in the first embodiment, at the time of executing the concentration measurement operation when the osmosis membrane 86 of the concentration meter 80 is in the dry state, the endoscope reprocessor 1 of the present embodiment increases the amount of the measurement target matter which passes through the osmosis membrane 86 by generating the second state and, thereby, can execute concentration measurement of the measurement target liquid 100 by the concentration meter 80 without delay even if the osmosis membrane 86 is in the dry state.

Note that the present invention is not limited to the embodiments described before and can be appropriately changed within a range not departing from the spirit or idea of the invention that can be read from the Claims and the whole specification; and an endoscope reprocessor in which such a change has been made is also included in the technical scope of the present invention.

According to the present invention, it is possible to realize an endoscope reprocessor capable of executing concentration measurement without delay even when an osmosis membrane of a concentration meter is in the dry state.

What is claimed is:

1. An endoscope reprocessor provided with a processing tank capable of arranging an endoscope therein, the endoscope reprocessor being configured to perform reprocessing of the endoscope in the processing tank using a measurement target liquid, the endoscope reprocessor comprising:
   a concentration meter configured to measure a concentration of the measurement target liquid, the concentration meter comprising:
      a housing including a hollow;
      an electrode accommodated in the hollow;
      an osmosis membrane covering the hollow; and
      internal liquid stored in the hollow and connecting the electrode and the osmosis membrane;
   a tank configured to store the measurement target liquid and attachably and detachably hold the concentration meter so that the osmosis membrane is in contact with the measurement target liquid;
   one or more pumps configured to adjust an air pressure of an inside of the hollow and an air pressure of an inside of the tank; and
   a controller configured to control the one or more pumps to enter a first state in which the pressure of the internal liquid is a first pressure, and the pressure of the measurement target liquid is a second pressure, and a second state in which the pressure of the internal liquid is a third pressure lower than the first pressure, and the pressure of the measurement target liquid is a fourth pressure lower than the second pressure.

2. The endoscope reprocessor according to claim 1, wherein the controller is further configured to:
   determine dryness of the osmosis membrane; and
   control the one or more pumps so that the first state is entered when it is determined that the osmosis membrane is not dry at time of concentration measurement by the concentration meter, and the second state is entered when it is determined that the osmosis membrane is dry.

3. The endoscope reprocessor according to claim 1, wherein the measurement target liquid comprises disinfecting liquid.

4. The endoscope reprocessor according to claim 1, wherein
   the one or more pumps comprises one pump;
   the one pump discharges air in the inside of the tank or sends out air into the inside of the tank; and
   the housing is provided with a ventilation portion configured to cause the inside of the hollow and the inside of the tank to communicate with each other.

5. The endoscope reprocessor according to claim 1, wherein
   the one or more pumps comprises two pumps;
   one of the two pumps discharges air in the inside of the tank or sends out air into the inside of the tank; and
   an other of the two pumps discharges air in the inside of the hollow or sends out air into the inside of the hollow.

6. The endoscope reprocessor according to claim 5, wherein the controller is further configured to:
   determine the air pressure of the inside of the hollow; and
   determine the air pressure of the inside of the tank; and
   control the two pumps so that the first pressure and the second pressure are equalized in the first state, and the third pressure and the fourth pressure are equalized in the second state.

7. The endoscope reprocessor according to claim 2, wherein the controller is further configured to control the one or more pumps before the concentration measurement by the concentration meter to maintain the second state for a predetermined time period when it is determined that the osmosis membrane is dry.

8. The endoscope reprocessor according to claim 7, wherein the predetermined time period is 5 seconds or more.

* * * * *